(12) United States Patent
Anderson

(10) Patent No.: US 8,354,837 B2
(45) Date of Patent: Jan. 15, 2013

(54) SYSTEM AND METHOD FOR ELECTROMAGNETIC TRACKING OPERABLE WITH MULTIPLE COIL ARCHITECTURES

(75) Inventor: Peter Traneus Anderson, Andover, MA (US)

(73) Assignee: GE Medical Systems Global Technology Company LLC, Waukesha, WI (US)

( * ) Notice: Subject to any disclaimer, the term of this patent is extended or adjusted under 35 U.S.C. 154(b) by 2623 days.

(21) Appl. No.: 10/670,054

(22) Filed: Sep. 24, 2003

(65) Prior Publication Data

US 2005/0065433 A1    Mar. 24, 2005

(51) Int. Cl.
G01B 7/14 (2006.01)
A61B 5/06 (2006.01)

(52) U.S. Cl. .................... 324/207.17; 600/424
(58) Field of Classification Search ............ None
See application file for complete search history.

(56) References Cited

U.S. PATENT DOCUMENTS

| | | |
|---|---|---|
| 3,868,565 A | 2/1975 | Kuipers |
| 3,983,474 A | 9/1976 | Kuipers |
| 4,054,881 A | 10/1977 | Raab |
| 4,176,662 A | 12/1979 | Frazer |
| 4,613,866 A | 9/1986 | Blood |
| 4,618,822 A | 10/1986 | Hansen |
| 4,622,644 A | 11/1986 | Hansen |
| 4,642,786 A | 2/1987 | Hansen |
| 4,710,708 A | 12/1987 | Rorden et al. |
| 4,737,794 A | 4/1988 | Jones |
| 4,742,356 A | 5/1988 | Kuipers |
| 5,099,845 A | 3/1992 | Besz et al. |
| 5,211,165 A | 5/1993 | Dumoulin et al. |
| 5,251,635 A | 10/1993 | Dumoulin et al. |
| 5,255,680 A | 10/1993 | Darrow |
| 5,265,610 A | 11/1993 | Darrow |
| 5,307,072 A | 4/1994 | Jones |
| 5,377,678 A | 1/1995 | Dumoulin et al. |
| 5,425,367 A | 6/1995 | Shapiro |
| 5,425,382 A | 6/1995 | Golden et al. |
| 5,437,277 A | 8/1995 | Dumoulin |
| 5,443,066 A | 8/1995 | Dumoulin et al. |
| 5,445,150 A | 8/1995 | Dumoulin et al. |

(Continued)

FOREIGN PATENT DOCUMENTS

EP    0543551    5/1993

(Continued)

OTHER PUBLICATIONS

Peter T. Anderson, A Source of Accurately Calculable Quasi-Static Magnetic Fields, Oct. 2001.

(Continued)

*Primary Examiner* — Jay M Patidar
(74) *Attorney, Agent, or Firm* — McAndrews, Held & Malloy, Ltd.; William Baxter

(57) ABSTRACT

Certain embodiments of the present invention provide a system and method for software configurable electromagnetic tracking. Certain embodiments of the system include a transmitter and/or a receiver for measuring a position in a coordinate system. The system also includes tracker electronics for determining position of the transmitter and/or receiver using information from the transmitter and/or receiver. The tracker electronics are configurable for a plurality of tracking system architectures. The tracker electronics may generate a processing scheme for a tracking system architecture. Additionally, the tracker electronics may simultaneously support a plurality of tracking system architectures. The tracker electronics may be modular, configurable tracker electronics. The tracker electronics may use software to generate support for a plurality of tracking system architectures.

14 Claims, 5 Drawing Sheets

U.S. PATENT DOCUMENTS

| | | | |
|---|---|---|---|
| 5,517,195 | A | 5/1996 | Narlow et al. |
| 5,558,091 | A | 9/1996 | Acker |
| 5,570,021 | A | 10/1996 | Dachniwskyj |
| 5,592,939 | A | 1/1997 | Martinelli |
| 5,622,169 | A | 4/1997 | Golden et al. |
| 5,676,673 | A | 10/1997 | Ferre et al. |
| 5,747,996 | A | 5/1998 | Fuchs |
| 5,803,089 | A | 9/1998 | Ferre et al. |
| 5,829,444 | A | 11/1998 | Ferre et al. |
| 5,873,822 | A | 2/1999 | Ferre et al. |
| 5,876,325 | A | 3/1999 | Mizuno et al. |
| 5,967,980 | A | 10/1999 | Ferre et al. |
| 6,039,701 | A | 3/2000 | Sliwa et al. |
| 6,052,610 | A | 4/2000 | Koch |
| 6,059,718 | A | 5/2000 | Taniguchi |
| 6,073,043 | A | 6/2000 | Schneider |
| 6,129,667 | A | 10/2000 | Dumoulin |
| 6,129,668 | A | 10/2000 | Haynor et al. |
| 6,175,756 | B1 | 1/2001 | Ferre et al. |
| 6,177,792 | B1 | 1/2001 | Govari |
| 6,188,355 | B1 | 2/2001 | Gilboa |
| 6,201,987 | B1 | 3/2001 | Dumoulin |
| 6,226,547 | B1 | 5/2001 | Lockhart |
| 6,230,038 | B1 | 5/2001 | von Gutfeld et al. |
| 6,233,476 | B1 | 5/2001 | Strommer et al. |
| 6,246,898 | B1 | 6/2001 | Smith |
| 6,259,372 | B1 | 7/2001 | Taranowski et al. |
| 6,289,233 | B1 | 9/2001 | Dumoulin et al. |
| 6,341,231 | B1 | 1/2002 | Ferre et al. |
| 6,369,564 | B1 | 4/2002 | Khalfin et al. |
| 6,374,131 | B1 | 4/2002 | Tomita et al. |
| 6,374,134 | B1 | 4/2002 | Bladen |
| 6,427,079 | B1 | 7/2002 | Schneider et al. |
| 6,445,943 | B1 | 9/2002 | Ferre et al. |
| 6,456,074 | B1 | 9/2002 | Minas |
| 6,459,882 | B1 | 10/2002 | Palermo |
| 6,463,039 | B1 | 10/2002 | Ricci |
| 6,472,975 | B1 | 10/2002 | Beigel et al. |
| 6,492,816 | B1 | 10/2002 | Feenan |
| 6,490,475 | B1 | 12/2002 | Seeley et al. |
| 6,636,757 | B1 | 10/2003 | Jascob et al. |
| 6,774,624 | B2 | 8/2004 | Anderson et al. |
| 6,856,826 | B2 | 2/2005 | Seeley et al. |
| 6,856,827 | B2 | 2/2005 | Seeley et al. |
| 2002/0008516 | A1 | 1/2002 | Dietz |
| 2003/0184285 | A1* | 10/2003 | Anderson et al. ........ 324/207.17 |
| 2005/0003757 | A1* | 1/2005 | Anderson ................... 455/41.1 |
| 2005/0012597 | A1 | 1/2005 | Anderson |
| 2005/0024043 | A1* | 2/2005 | Govari ..................... 324/207.17 |
| 2005/0059883 | A1* | 3/2005 | Peterson ....................... 600/424 |

FOREIGN PATENT DOCUMENTS

| | | |
|---|---|---|
| EP | 1193507 A | 4/2002 |
| EP | 1493384 | 1/2005 |
| JP | 01303140 A | 12/1989 |
| JP | 09000507 A | 1/1997 |

OTHER PUBLICATIONS

Tom Ahlkvist Scharfeld, An Analysis of the Fundamental Constraints on Low Cost Passive Radio-Frequency Identification System Design, Aug. 2001.

Jan. 19, 2005 Communication regarding counterpart EP App. No. 04255755.3-1524.

Nov. 17, 2005 Communication regarding counterpart EP App. No. 04255755.3-1524.

Jul. 7, 2006 Communication regarding counterpart EP App. No. 04255755.3-1524.

•Sep. 14 and 17, 2007 Communication regarding counterpart EP App. No. 04255755.3-1524.

* cited by examiner

FIG. 4

| 10
Wired ISCA
architecture | 20
Wireless transmitter
ISCA architecture |

| 30
Wired single coil
transmitter
architecture | 40
Wireless single coil
transmitter
architecture |

FIG. 5

51
Industry-standard coil architecture (ISCA) using three colocated orthogonal quasi-dipole transmitter coils and three colocated quasi-dipole receiver coils

52
Second tracking system coil architecture using non-dipole, non-colocated transmitter coils and three colocated quasi-dipole receiver coils

53
Third tracking system coil architecture using an array of six or more transmitter coils and one or more quasi-dipole receiver coils

54
Fourth tracking system coil architecture using a single quasi-dipole transmitter coil and an array of six or more receiver coils

SYSTEM AND METHOD FOR ELECTROMAGNETIC TRACKING OPERABLE WITH MULTIPLE COIL ARCHITECTURES

RELATED APPLICATIONS

[Not Applicable]

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

The present invention generally relates to an electromagnetic tracking system. In particular, the present invention relates to a software configurable electromagnetic tracking system accommodating a plurality of coil architectures.

Many medical procedures involve a medical instrument, such as a drill, a catheter, scalpel, scope, shunt or other tool. In some cases, a medical imaging or video system may be used to provide positioning information for the instrument. However, medical practitioners often do not have the use of medical imaging systems when performing medical procedures. The use of medical imaging systems for instrument tracking may be limited for health and safety reasons (e.g., radiation dosage concerns), financial limitations, physical space restrictions, and other concerns, for example.

Medical practitioners, such as doctors, surgeons, and other medical professionals, often rely upon technology when performing a medical procedure, such as image-guided surgery or examination. A tracking system may provide positioning information for the medical instrument with respect to the patient or a reference coordinate system, for example. A medical practitioner may refer to the tracking system to ascertain the position of the medical instrument when the instrument is not within the practitioner's line of sight. A tracking system may also aid in pre-surgical planning.

The tracking or navigation system allows the medical practitioner to visualize the patient's anatomy and track the position and orientation of the instrument. The medical practitioner may use the tracking system to determine when the instrument is positioned in a desired location. The medical practitioner may locate and operate on a desired or injured area while avoiding other structures. Increased precision in locating medical instruments within a patient may provide for a less invasive medical procedure by facilitating improved control over smaller instruments having less impact on the patient. Improved control and precision with smaller, more refined instruments may also reduce risks associated with more invasive procedures such as open surgery.

Tracking systems may also be used to track the position of items other than medical instruments in a variety of applications. That is, a tracking system may be used in other settings where the position of an instrument in an object or an environment is difficult to accurately determine by visual inspection. For example, tracking technology may be used in forensic or security applications. Retail stores may use tracking technology to prevent theft of merchandise. In such cases, a passive transponder may be located on the merchandise. A transmitter may be strategically located within the retail facility. The transmitter emits an excitation signal at a frequency that is designed to produce a response from a transponder. When merchandise carrying a transponder is located within the transmission range of the transmitter, the transponder produces a response signal that is detected by a receiver. The receiver then determines the location of the transponder based upon characteristics of the response signal.

Tracking systems are also often used in virtual reality systems or simulators. Tracking systems may be used to monitor the position of a person in a simulated environment. A transponder or transponders may be located on a person or object. A transmitter emits an excitation signal and a transponder produces a response signal. The response signal is detected by a receiver. The signal emitted by the transponder may then be used to monitor the position of a person or object in a simulated environment.

Tracking systems may be ultrasound, inertial position, or electromagnetic tracking systems, for example. Electromagnetic tracking systems may employ coils as receivers and transmitters. Typically, an electromagnetic tracking system is configured in an industry-standard coil architecture (ISCA). ISCA 51 uses three colocated orthogonal quasi-dipole transmitter coils and three colocated quasi-dipole receiver coils. Other systems 52 may use three large, non-dipole, non-colocated transmitter coils with three colocated quasi-dipole receiver coils. Another tracking system architecture 53 uses an array of six or more transmitter coils spread out in space and one or more quasi-dipole receiver coils. Alternatively, a tracking system coil architecture 54 using a single quasi-dipole transmitter coil may be used with an array of six or more receivers spread out in space.

The ISCA tracker architecture uses a three-axis dipole coil transmitter and a three-axis dipole coil receiver. Each three-axis transmitter or receiver is built so that the three coils exhibit the same effective area, are oriented orthogonally to one another, and are centered at the same point. An example of a dipole coil trio with coils in X, Y, and Z directions spaced approximately equally about a center point is shown in FIG. 3. If the coils are small enough compared to a distance between the transmitter and receiver, then the coil may exhibit dipole behavior. Magnetic fields generated by the trio of transmitter coils may be detected by the trio of receiver coils. Using three approximately concentrically positioned transmitter coils and three approximately concentrically positioned receiver coils, for example, nine parameter measurements may be obtained. From the nine parameter measurements and one known position or orientation parameter, a position and orientation calculation may determine position and orientation information for each of the transmitter coils with respect to the receiver coil trio with three degrees of freedom.

Different coil architectures involve different system components and requirements. For example, different coil architectures include different numbers of transmitter coil drivers, different number of receiver coil preamp channels, different signal processing, different mathematical models of coils, and/or different position-and-orientation calculation algorithms.

Currently, a tracking system may only use one coil architecture. Changing coil architecture requires replacing the entire tracking system, not only the coils. Existing tracking systems only permit simultaneous tracking of multiple receiver assemblies when all receiver assemblies use the same coil architecture. Therefore, in order to provide a multi-purpose tracking system for medical applications, such as image-guided surgery, multiple tracker systems using various coil architectures must be installed in the medical system.

Thus, a tracking system that operates with various coil architectures would be highly desirable. Additionally, a tracking system that is easily adjustable and configurable would be highly desirable. There is a need for a software configurable electromagnetic tracking system accommodating a plurality of coil architectures. A need also exists for an electromagnetic surgical navigation system that allows surgical or other medical procedures to be performed in a less invasive manner.

BRIEF SUMMARY OF THE INVENTION

Certain embodiments of the present invention provide a system and method for software configurable electromagnetic tracking. Certain embodiments of the system include a transmitter for transmitting a signal, a receiver for receiving the signal from the transmitter, and tracker electronics for analyzing the signal received by the receiver. The tracker electronics accommodate a plurality of tracking system architectures for the transmitter and the receiver.

The tracker electronics may be configured by software to accommodate a plurality of tracking system architectures. The tracker electronics may store waveforms for a tracking system architecture in memory and/or may generate waveforms on demand. Additionally, the tracker electronics may store software for a tracking system architecture in memory and/or may generate software code on demand.

The tracker electronics may be modular tracker electronics. In an embodiment, the tracker electronics determine position and/or orientation of the transmitter based on the receiver. The tracker electronics may also determine position and/or orientation of the receiver based on the transmitter.

Certain embodiments of the method include selecting a tracker configuration for components in an electromagnetic tracker, generating a processing scheme for the tracker configuration, and applying the processing scheme to the components in the electromagnetic tracker. The processing scheme may be generated on demand. The processing scheme may be generated using software and/or a configurable processor. The processing scheme may be stored in memory. The method may also include determining a position and/or an orientation of at least one component in the electromagnetic tracker.

Certain embodiments provide a configurable electromagnetic tracking system. In an embodiment, the system includes a transmitter and/or a receiver for measuring a position in a coordinate system. The system also includes tracker electronics for determining position of the transmitter and/or receiver using information from the transmitter and/or receiver. The tracker electronics are configurable for a plurality of tracking system architectures. The tracker electronics may generate a processing scheme for a tracking system architecture. Additionally, the tracker electronics may simultaneously support a plurality of tracking system architectures. The tracker electronics may be modular, configurable tracker electronics. The tracker electronics may use software to generate support for a plurality of tracking system architectures.

BRIEF DESCRIPTION OF SEVERAL VIEWS OF THE DRAWINGS

FIG. 4 illustrates a simplified diagram of a wired ISCA architecture, a wireless transmitter ISCA architecture, a wired single coil transmitter architecture, and a wireless single coil transmitter architecture, according to an embodiment of the present invention.

FIG. 5 illustrates a simplified diagram of an industry-standard coil architecture (ISCA), a second tracking system coil architecture, a third tracking system coil architecture, and a fourth tracking system coil architecture, according to an embodiment of the present invention.

Figure 1:
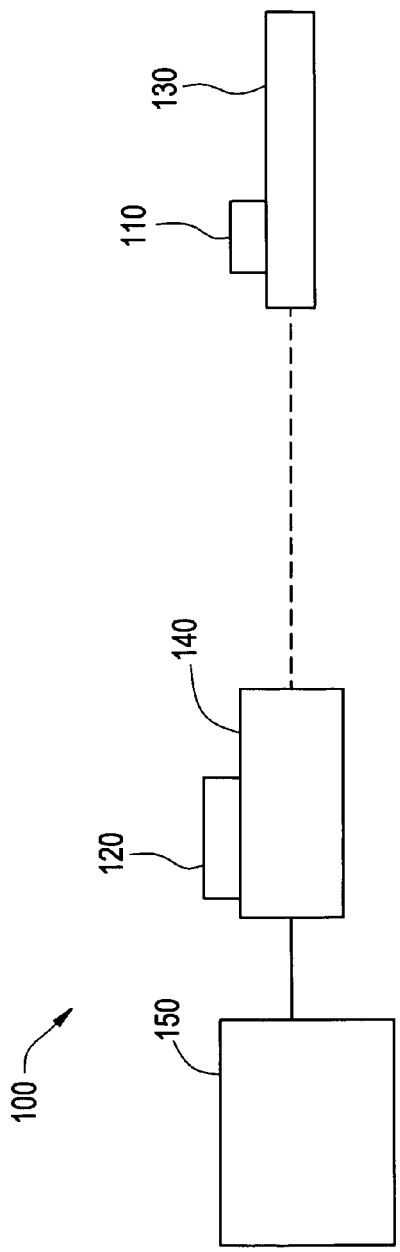
FIG. 1 illustrates an electromagnetic tracking system used in accordance with an embodiment of the present invention.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

For the purpose of illustration only, the following detailed description references an embodiment of an electromagnetic tracking system used with an image-guided surgery system. It is understood that the present invention may be used with other imaging systems and other applications.

FIG. 1 illustrates an electromagnetic tracking system 100 used in accordance with an embodiment of the present invention. The tracking system 100 includes a transmitter 110, a receiver assembly 120, an instrument 130, an instrument guide 140, and a tracker electronics 150. In an embodiment, the transmitter 110 is positioned on the instrument 130. The receiver assembly 120 is located remotely from the instrument 130 and the transmitter 110. The instrument guide 140 is used to control the instrument 130.

In an embodiment, the receiver assembly 120 includes two receivers 122, 124. The receivers 122, 124 of the receiver assembly 120 may be receiver dipole coils or coil trios, for example. The receiver assembly 120 may be attached to the instrument guide 140. The instrument 130 may be a surgical drill or other medical instrument, for example. The instrument guide 140 may be a drill guide or other medical instrument guide, for example. In another embodiment, the instrument 130 with instrument guide 140 may be a tool that is indirectly controlled for applications wherein an operator's field of vision is obscured by an object.

The transmitter 110 may be a wired or wireless transmitter. In certain embodiments, the transmitter 110 is attached to the instrument 130. Alternatively, the transmitter 110 may be integrated with the instrument 130. Using the transmitter 110 and receiver assembly 120, the position of the instrument 130 is tracked with respect to the instrument guide 140 or other reference point, for example.

The system 100 may also include one or more additional transmitters (not shown) for use in instrument 130 tracking. The additional transmitter(s) may be wired or wireless transmitter(s). For example, a wireless second transmitter may be located on the instrument guide 140 or on the instrument 130. Alternatively, for example, a wired second transmitter may be located on the instrument guide 140. The second transmitter may be wired to the tracker electronics 150. A cable may be run from the second transmitter to the tracker electronics 150. The transmitter 110 and additional transmitter(s) may be tracked simultaneously from the receivers in the receiver assembly 120.

In an embodiment, the transmitter 110 may be an ISCA transmitter, such as an ISCA transmitter coil trio, for example. Software used with the tracker electronics 150 may be configured to accommodate the transmitter 110 and/or another wired or wireless transmitter. The transmitter 110 may draw power from the instrument 130 or may have a separate power source, for example. The transmitter 110 may be tracked from each of the receivers in the receiver assembly 120. Thus, certain embodiments use the transmitter 110 and the receiver assembly 120 to track the position of the instrument 130 with respect to the instrument guide 140.

In an embodiment, the tracker electronics 150 includes a Lucas 4650 processor, for example. The tracker electronics 150 may be integrated with the receiver assembly 120 or may be a separate module, for example. In an embodiment, the tracker electronics 150 resides on a receiver assembly 120 board to perform a Sum of Products (SOP) and other calculations on signal data. An SOP may be calculated using the following equation:

$$y = \sum_{n=1}^{k} a_n * x_n. \tag{1}$$

In an embodiment, the tracker electronics 150 may include a large number of transmitter coil drivers (to accommodate a large number of transmitter coils used simultaneously, for example). The tracker electronics 150 may also include a modular design permitting additional transmitter coil drivers to be added based on a coil architecture in use. Wireless transmitters have no direct, physical connection with the system 100 and may be added to the tracker electronics 150 with minimal effort.

Waveforms for transmitter coil drivers may be stored in a memory, such as a random access memory (RAM) or hard disk drive, or may be generated on-the-fly by a software-controlled signal generator, such as a direct digital synthesizer (DDS), for example. Driver waveforms may be changed for different coil architectures by changing data in the RAM or other memory storing the waveforms or by adjusting settings of the software-controlled generator.

Driver waveforms may be distinguished using sine waves of different frequencies, for example. A similar effect may be accomplished by using waveforms that are nonzero at different times or by using a spread-spectrum code division technique.

The tracker electronics 150 may include a large number of receiver coil preamplifier channels (to accommodate a large number of transmitter coils used simultaneously, for example). Alternatively, the tracker electronics 150 may include a modular design allowing additional receiver coil drivers to be added based on a coil architecture(s) in use. Wireless receiver coil preamplifer channels may be added as well.

Signals emitted from receiver preamplifiers are transmitted to analog-to-digital converters (ADCs). The ADCs digitize the receiver preamplifier signals. Digital signals output from the ADCs are processed by software. In an embodiment, the software is stored in RAM or other memory. The software extracts desired frequency components of the digital signals. The frequency components may be further processed to calculate the position and orientation of the receiver assembly or assemblies, for example.

Since the software is stored in memory, algorithms, coil models, and processing schemes included in or generated by the software may be easily altered by modifying, reconfiguring, or replacing the software, for example. Software may be modified to accommodate various coil architectures or system parameters. In an embodiment, algorithms for multiple coil architectures may be loaded in memory. Multiple coil architecture algorithms and models, for example, allow multiple coil architectures to be run simultaneously. Rapid switching between architectures may also be facilitated using multiple configurations. In an embodiment, the tracker electronics 150 may register multiple coordinate systems for multiple architectures.

For example, an ISCA architecture and a single transmitter coil architecture may be running simultaneously in the system 100. A position and orientation of an ISCA receiver are determined with respect to an ISCA transmitter. A position and orientation of a single coil transmitter (with less roll, for example) are determined with respect to a single transmitter coil receiver coil array (a spread-out coil array, for example).

Additionally, the receiver coil array may be used to track the ISCA transmitter coil trio. The receiver coil array may be used to determine position and orientation information (including roll, for example) of the ISCA transmitter with respect to the receiver coil array. Then, the position and orientation of the ISCA receiver with respect to the receiver coil array may be determined. Similarly, an ISCA receiver may be tracked with respect to a transmitter coil array (a spread-out transmitter coil array, for example).

The following examples illustrate various exemplary coil architectures that may be configured for use in the system 100. Example coil architectures include a wired ISCA architecture 10, a wireless transmitter ISCA architecture 10, a wired single coil transmitter architecture 30, and a wireless single coil transmitter architecture 40. In a wired ISCA architecture 10, three ISCA drivers drive a trio of transmitter coils. Four receiver coil trios each drive three receiver preamplifier channels. In a wireless transmitter ISCA architecture 20, an added wireless driver drives the three transmitter coils. Each of four receiver coil trios drives three receiver preamplifier channels in an array of twelve receiver preamplifier channels. For a single coil wired transmitter architecture 30, an ISCA driver may be used to drive the single transmitter coil. A twelve coil receiver assembly drives twelve receiver preamplifier channels. For a single coil wireless transmitter architecture 40, a wireless driver drives the single transmitter coil. A twelve coil receiver assembly drives twelve receiver preamplifier channels.

Mutual inductance may be used in the electromagnetic tracking system to identify the positions of components in the system. Mutual inductance may allow the system to be divided into two parts: coils and electronics. Determining mutual inductance involves a physical design of the coils and a geometrical relationship between the coils but may not use details of the electronics used to measure the mutual inductance. Additionally, mutual inductance does not depend on which coil receives an applied current.

In addition to the electronics used to measure mutual inductance, a system including one transmitter coil and one receiver coil forms a four-terminal two-port network. A varying current injected into one coil induces a voltage in the other coil. The induced voltage V is proportional to the rate of change of the applied current I:

$$V = L_m (dI/dt) \tag{2},$$

wherein $L_m$ represents mutual inductance. $L_m$ is based on the geometry of the coils (closed circuits). $L_m$ is a ratio independent of applied current waveform or frequency. Thus, $L_m$ is a well-defined property that may be measured with reasonable precision.

In an embodiment, a positional relationship between the receiver coils in the receiver assembly 120 is known. The receiver coils receive the signal transmitted by the wireless transmitter coil. The position and orientation of the wireless transmitter 110 relative to a reference coordinate system may then be determined using the mutual inductance between the receiver and transmitter coils and the positional relationship between the receiver coils. The resulting tracked position and orientation of the wireless transmitter 110 attached to the drill in relation to the receiver assembly 120 on the drill guide may be used to help a user manipulate the drill inside the patient's body. Positioning information may help prevent injury to the patient and minimize unnecessary risk.

In certain embodiments, the electromagnetic tracking system 100 allows for the object being tracked to move freely without being limited by connections with a transmitter 110 or receiver 122, 124. To reduce the bulk associated with attaching a battery or other power source to a transponder, passive transponders may employ a coil as a means of coupling with and receiving power from other devices.

In certain embodiments, ratios between fields are measured, rather than absolute values. Precise ratios may be easier to obtain than precise absolute values. Five of six degrees of freedom for position and orientation measurements may be determined from ratios of received magnetic fields or mutual inductances, for example. Range (e.g., a distance from a receiver to a transmitter) may not be determined without a field strength or mutual inductance value.

In an embodiment, two receiver coil trios, such as ISCA receiver coil trios, are used to determine range. Position and orientation parameters, aside from range, may be determined using magnetic field or mutual inductance ratio measurements from the six receivers in the two receiver coil trios. Additionally, a ratio of the ranges between the two receiver coil trios and the transmitter coil trio may be determined. Thus, a triangle is formed between the transmitter and receiver coil trios. The three angles of the triangle may be determined by ratio measurements. Additionally, a ratio of the two ranges is also determined. Using the three angles and the ratio of the two sides, the ratios of all three sides of the triangle may be determined. The side of the triangle that represents a distance between the two receiver coil trios may be determined based on construction of the receiver assembly 120. Thus, by triangulation, the ranges between the two receivers 122, 124 and the transmitter 110 may be determined (i.e., the remaining two sides of the triangle).

Figure 2:
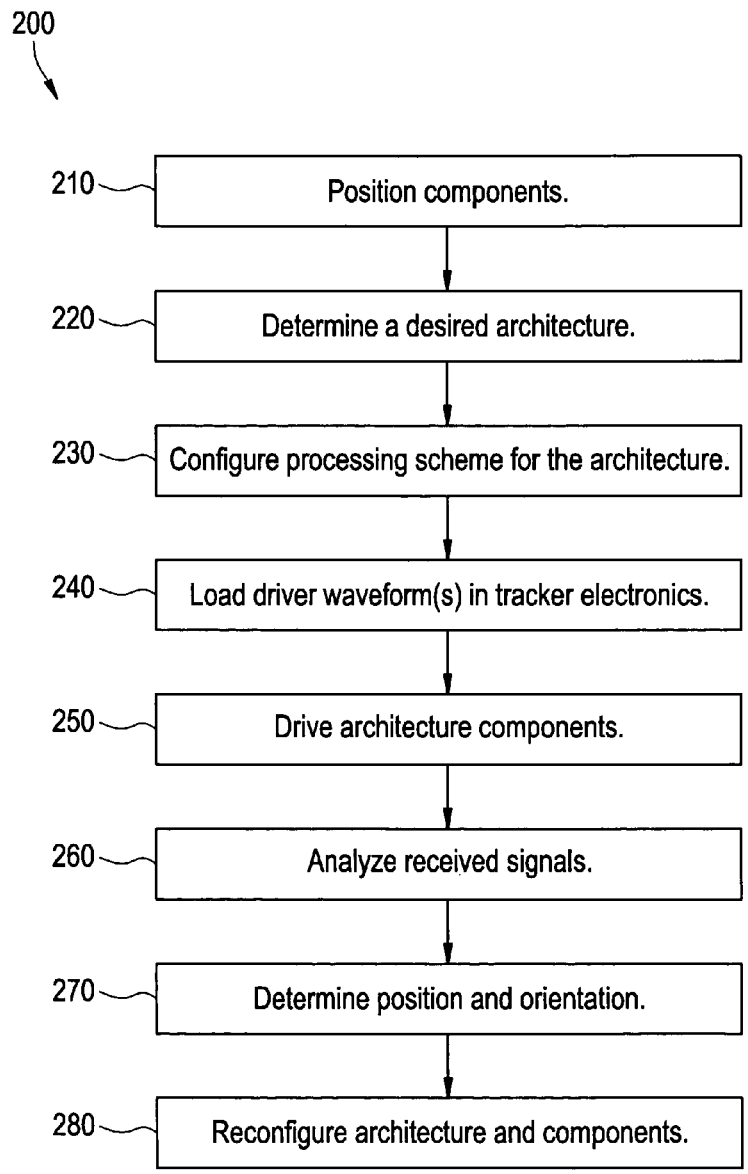
FIG. 2 shows a flow diagram for a method for configuring a tracking system used in accordance with an embodiment of the present invention.
Figure 3:
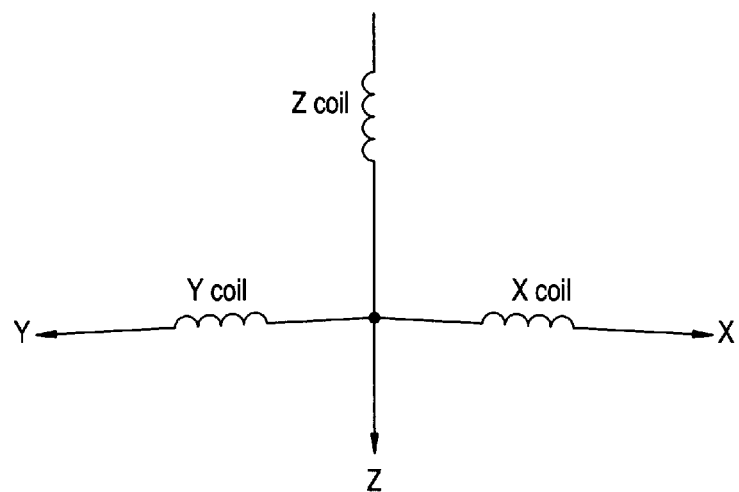
FIG. 3 illustrates a dipole coil trio used in accordance with an embodiment of the present invention.

FIG. 2 shows a flow diagram for a method 200 for configuring a tracking system used in accordance with an embodiment of the present invention. First, at step 210, components, such as the transmitter 110 and the receiver assembly 120, are positioned. Coils, for example, in the transmitter 110 and/or the receiver assembly 120 may be adjusted in a desired configuration. For example, a trio of wireless transmitter coils may be positioned with respect to an array of wired receiver coil trios.

Then, at step 220, a desired architecture is determined. For example, an operator selects an ISCA coil architecture for the system. Alternatively, the tracker electronics 150 or other processor may detect that an ISCA architecture is in use.

Next, at step 230, a model and/or processing scheme for the current architecture are configured. For example, software implementing an ISCA coil architecture and tracking algorithms for an ISCA architecture are configured in the tracker electronics 150. At step 240, driver waveform(s) for the architecture are loaded in the tracker electronics 150. Software configured for the architecture may also be loaded in the tracker electronics 150. In an embodiment, the appropriate software and driver waveforms are stored in RAM for use by the tracker electronics 150. In another embodiment, driver waveforms and software are generated on the fly by the tracker electronics 150.

Then, at step 250, the waveforms are used to drive the components in the architecture. For example, driver waveforms are used to drive coils in the selected architecture. Next, at step 260, received signals are analyzed. For example, receiver coils receive signals or measurements, such as mutual inductance, magnetic fields, or current, from transmitter coils and transmit the received signals to the tracker electronics 150 for analysis. Then, at step 270, a position and orientation of a transmitter and/or receiver are determined. For example, signal ratios and/or triangulation between a transmitter and receivers may be used to determine position and orientation information.

At step 280, transmitter and/or receiver components may be changed and a new architecture may be configured. For example, components in a tracking system may be changed from an ISCA coil trio configuration to a single wireless transmitter coil architecture. Alternatively, multiple architectures may be supported simultaneously by the tracker electronics 150. For example, the tracker electronics may store and/or generate driver waveforms and operational information for both wired and wireless ISCA architectures.

For example, a wired transmitter coil trio and a wired receiver coil trio may be positioned in a wired ISCA configuration. The tracker electronics 150 detect a wired ISCA architecture. Then, ISCA coil drivers are generated to drive the transmitter coils. Data is received at the receiver coils and processed by the tracker electronics 150 to determine position and orientation of the ISCA transmitter in relation to the ISCA receiver. Next, an operator adds a wireless transmitter. The operator selects a wireless ISCA mode of operation. The wireless coil drivers are loaded into RAM. The tracker electronics 150 drives both the wired and wireless transmitter coils to determine position and orientation information. Thus, the tracker electronics 150 supports multiple architectures simultaneously to improve flexibility and accuracy of system performance and position and orientation determination.

Thus, certain embodiments of the present invention provide a system and method which permit a tracking system to operate with various coil architectures. In certain embodiments, the tracking system may operate with various coil architectures at different times and/or simultaneously. Certain embodiments provide a software-defined tracking system that accommodates a plurality of tracker coil architectures.

Certain embodiments simplify a tracking system for use in a multiple-application system, such as an image-guided surgery system. Certain embodiments allow existing tracking systems to be retrofitted for new tracker coil architectures without a loss of functionality. Software upgrades and replacement and/or additional coils may be used to modify current systems to accommodate multiple architectures at reduced cost without modification of tracker hardware. Thus, certain embodiments allow existing systems to be upgraded for new applications. Certain embodiments may open new retrofit markets for electromagnetic tracking systems.

Additionally, certain embodiments of the present invention may be used with a variety of tracking systems. For example, coils may be replaced with other types of magnetic field detectors, such as flux gate magnetometers, superconducting quantum interference devices (SQUID), or magnetoresistance sensors. A software-configurable tracking system may be programmed to accommodate a variety of tracking architectures.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A configurable electromagnetic tracking system, said system comprising:
   at least one of a transmitter and a receiver for measuring a position in a coordinate system;
   a single tracker electronics sub-system for determining position of said at least one of a transmitter and a receiver using information from said at least one of a transmitter and a receiver, wherein said single tracker electronics sub-system is used with a plurality of tracking system coil architectures.

2. The system of claim 1, wherein said tracker electronics sub-system generates a processing scheme for a tracking system coil architecture.

3. The system of claim 1, wherein said tracker electronics sub-system simultaneously supports the plurality of tracking system coil architectures.

4. The system of claim 1, wherein said tracker electronics sub-system comprises modular, configurable tracker electronics.

5. The system of claim 1, wherein said tracker electronics sub-system uses software to generate support for the plurality of tracking system coil architectures.

6. The system of claim 1, wherein said tracker electronics sub-system is configured by software to accommodate the plurality of tracking system coil architectures.

7. The system of claim 1, wherein said tracker electronics sub-system stores waveforms in memory for the plurality of tracking system coil architectures.

8. The system of claim 1, wherein said tracker electronics sub-system generates waveforms on demand for at least one of the plurality of tracking system coil architectures.

9. The system of claim 1, wherein said tracker electronics sub-system stores software in memory for the plurality of tracking system coil architectures.

10. The system of claim 1, wherein said tracker electronics sub-system generates software code on demand for at least one of the plurality of tracking system coil architectures.

11. The system of claim 1, wherein the at least one of a transmitter and a receiver includes both the transmitter and the receiver, and wherein the tracker electronics sub-system determines at least one of a position and an orientation of the receiver using information from the transmitter.

12. The system of claim 1, wherein the at least one of a transmitter and a receiver includes both the transmitter and the receiver, and wherein the tracker electronics sub-system determines at least one of a position and an orientation of the transmitter using information from the receiver.

13. The system of claim 1, wherein the plurality of tracking system coil architectures comprises:
   a first tracking system coil architecture that uses three colocated orthogonal dipole transmitter coils and three colocated quasi-dipole receiver coils; and
   a second tracking system coil architecture using non-dipole, non-colocated transmitter coils and three colocated quasi-dipole receiver coils.

14. The system of claim 13, wherein the plurality of tracking system coil architectures further comprises:
   a third tracking system coil architecture that uses an array of six or more transmitter coils and one or more quasi-dipole receiver coils; and
   a fourth tracking system coil architecture that uses a single quasi-dipole transmitter coil and an array of six or more receiver coils.

* * * * *